(12) United States Patent
Langley

(10) Patent No.: US 10,240,118 B2
(45) Date of Patent: Mar. 26, 2019

(54) SYSTEM FOR MONITORING GROWTH MEDIA

(71) Applicant: Mark Langley, Hebron, CT (US)

(72) Inventor: Mark Langley, Hebron, CT (US)

( * ) Notice: Subject to any disclaimer, the term of this patent is extended or adjusted under 35 U.S.C. 154(b) by 239 days.

(21) Appl. No.: 15/141,403

(22) Filed: Apr. 28, 2016

(65) Prior Publication Data
US 2016/0319235 A1  Nov. 3, 2016

Related U.S. Application Data

(60) Provisional application No. 62/155,221, filed on Apr. 30, 2015.

(51) Int. Cl.
| | | |
|---|---|---|
| *C12M 1/34* | (2006.01) | |
| *C12M 1/32* | (2006.01) | |
| *G01N 35/00* | (2006.01) | |

(52) U.S. Cl.
CPC ............ *C12M 41/46* (2013.01); *C12M 23/12* (2013.01); *C12M 41/36* (2013.01); *G01N 35/00871* (2013.01)

(58) Field of Classification Search
CPC ...... C12M 23/12; C12M 41/36; C12M 41/46; G01N 35/00871
See application file for complete search history.

(56) References Cited

U.S. PATENT DOCUMENTS

| | | | |
|---|---|---|---|
| 7,374,725 B2 | 5/2008 | Klein et al. | |
| 2004/0126876 A1* | 7/2004 | Ravin | ..................... B01L 3/508 |
| | | | 435/288.3 |
| 2005/0176155 A1* | 8/2005 | Klein | ..................... C12M 23/12 |
| | | | 436/163 |

OTHER PUBLICATIONS

U.S. Appl. No. 12/204,511, filed Dec. 25, 2008, Spittle et al.
U.S. Appl. No. 09/827,301, filed Jun. 6, 2002, Campbell et al.
U.S. Appl. No. 12/461,045, filed Jul. 22, 2010, Yan et al.
U.S. Appl. No. 14/079,022, filed Jun. 19, 2014, McGarr et al.

* cited by examiner

*Primary Examiner* — Gautam Prakash
*Assistant Examiner* — Lydia Edwards
(74) *Attorney, Agent, or Firm* — UConn IP Law Clinic; Anthony Analo

(57) ABSTRACT

A system for monitoring growth media within a controlled environment is provided and includes a well plate having a plate top and a plate side and defines at least one well cavity. The plate top includes a top opening and the plate side includes a side opening and the side opening is communicated with one of the at least one well cavity. The system includes a sensor assembly unit that includes a unit structure defining a reference material chamber containing a reference material, a sensor chamber having a chamber opening, and a base chamber. Additionally, the system includes a reference electrode communicated with the reference material and the base chamber. A media sensor is provided and is communicated with the chamber opening and a media sensor electrode communicated with the media sensor. The reference electrode and media sensor electrode are communicated with a processing device.

10 Claims, 21 Drawing Sheets

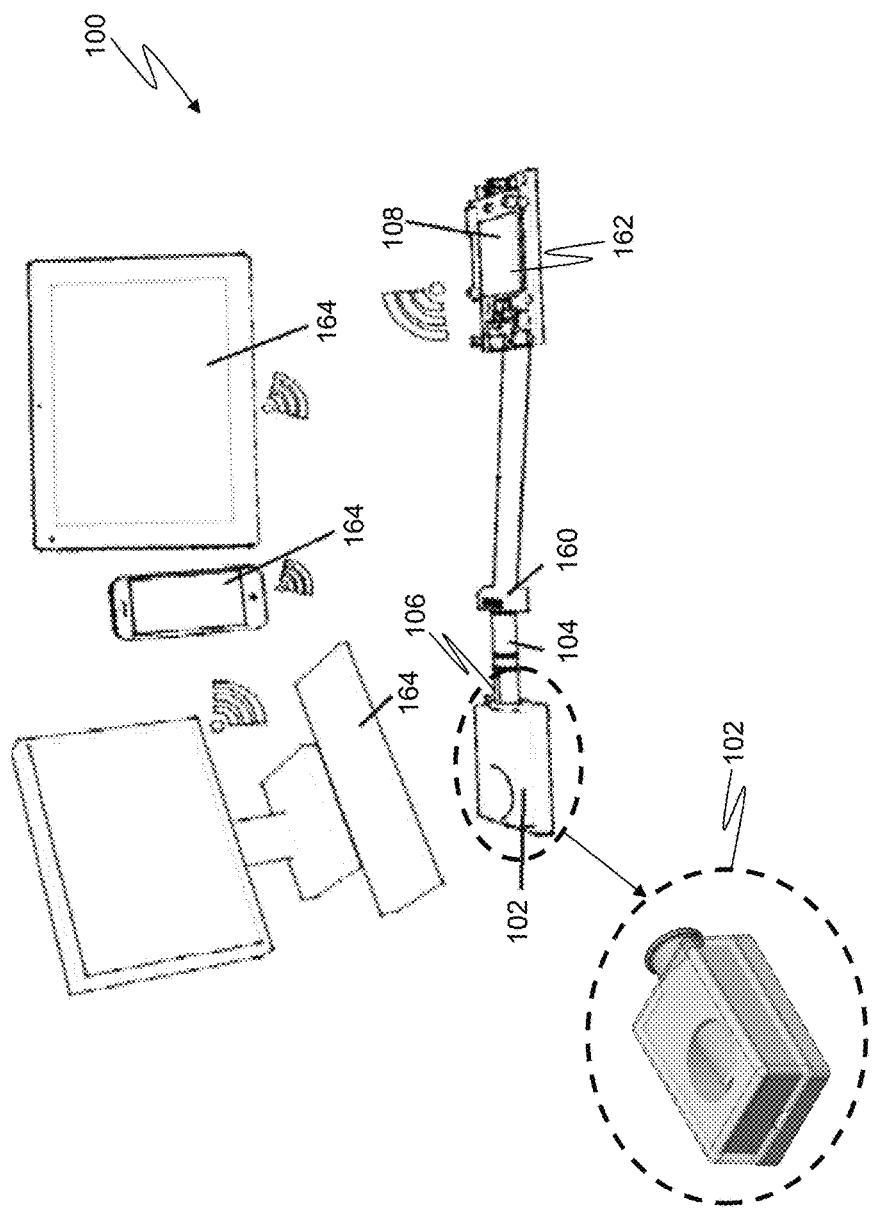

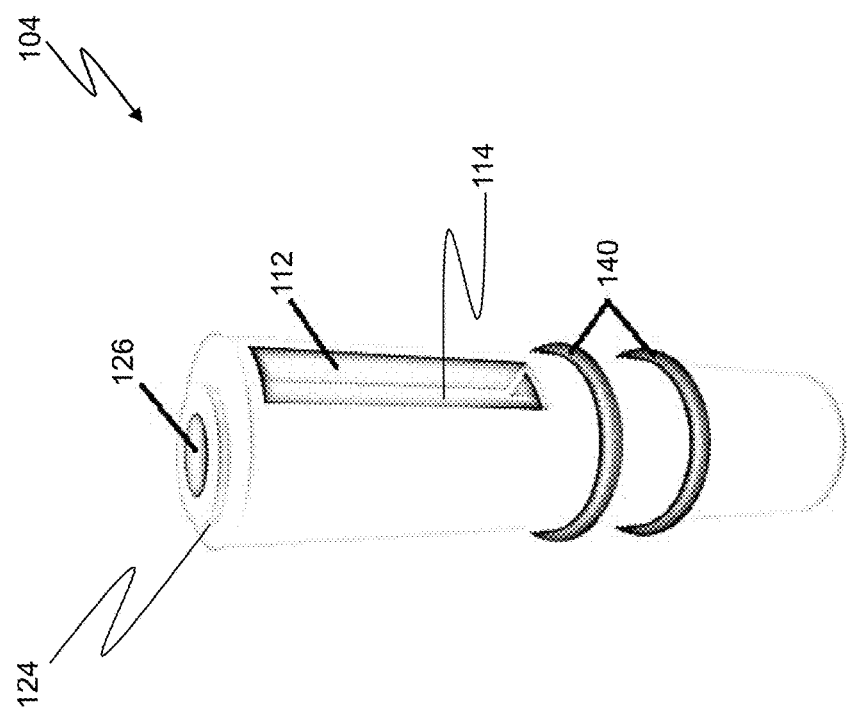

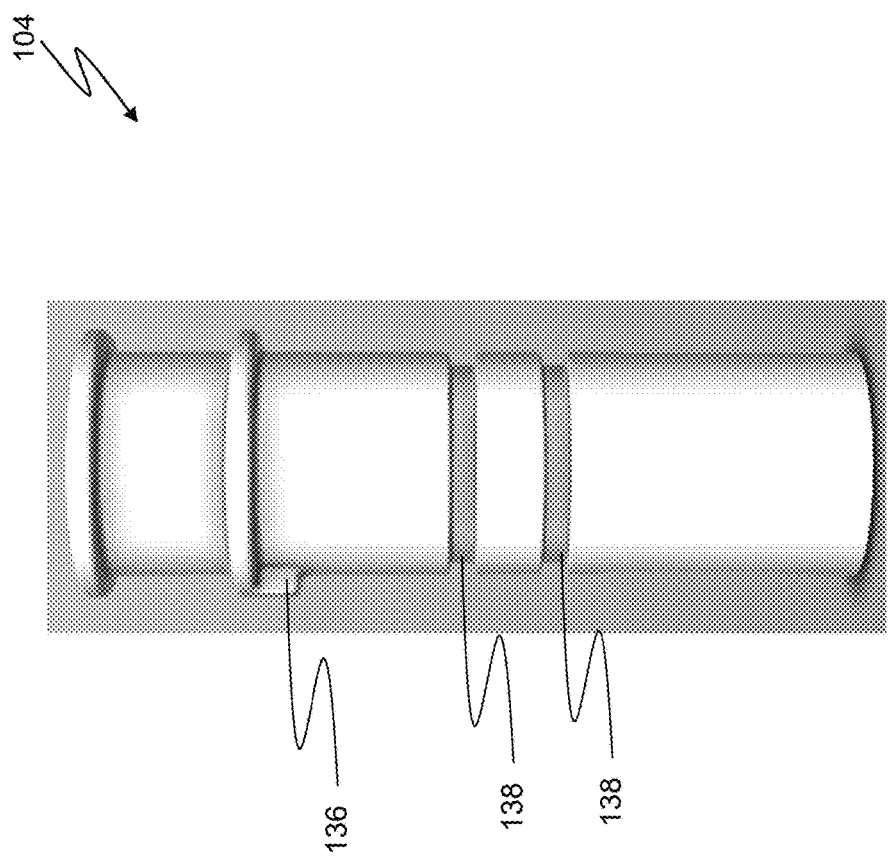

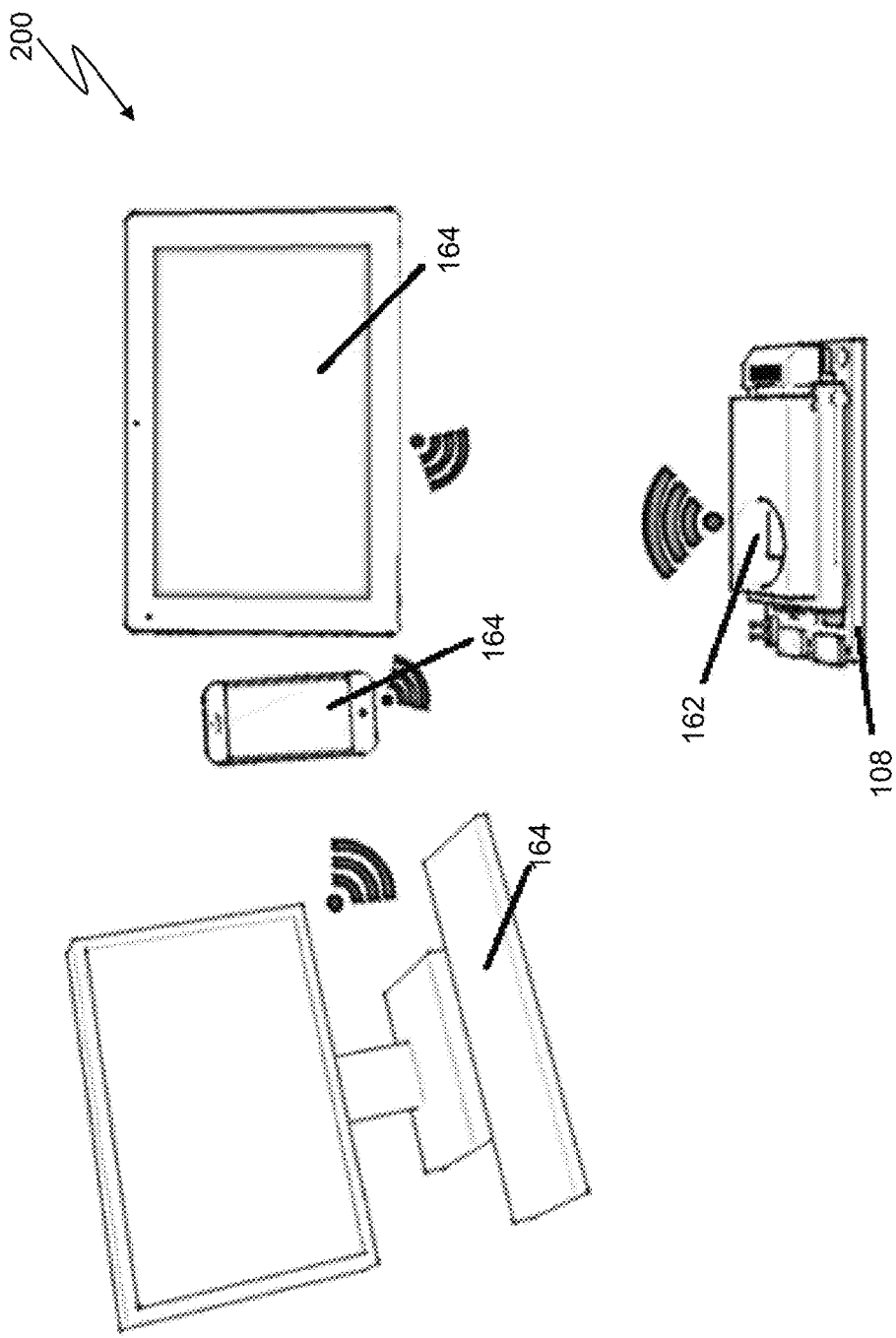

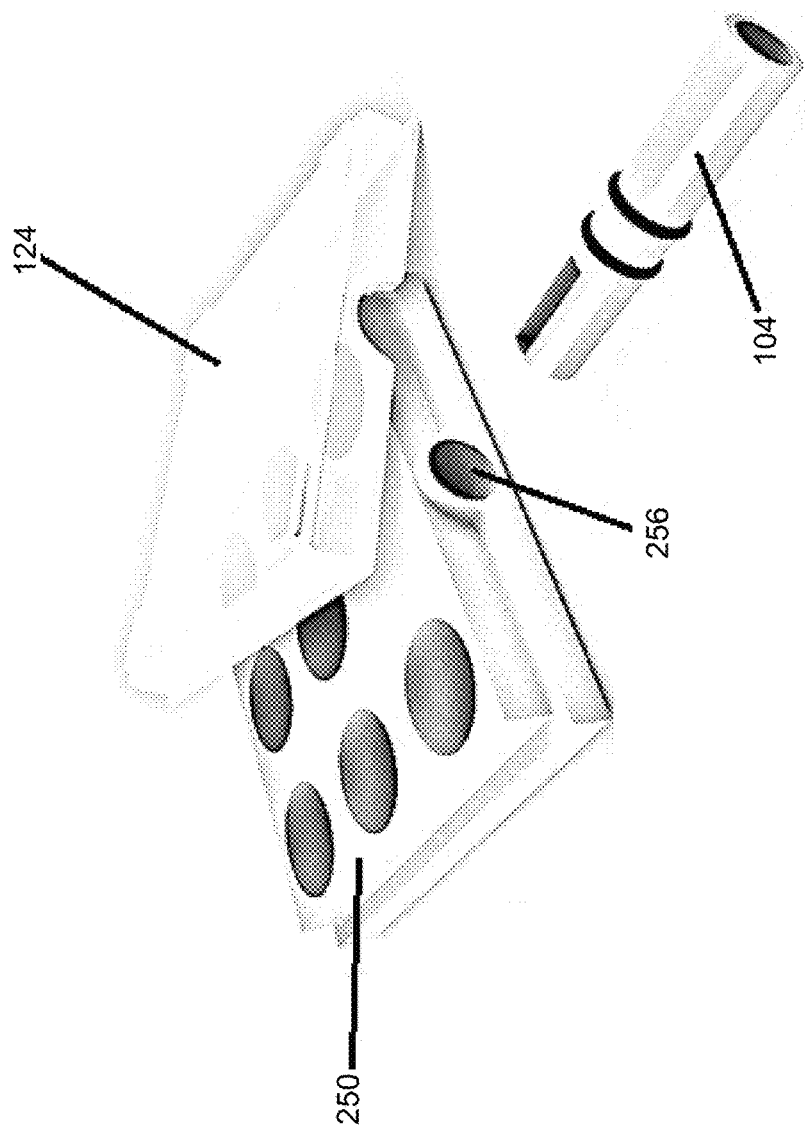

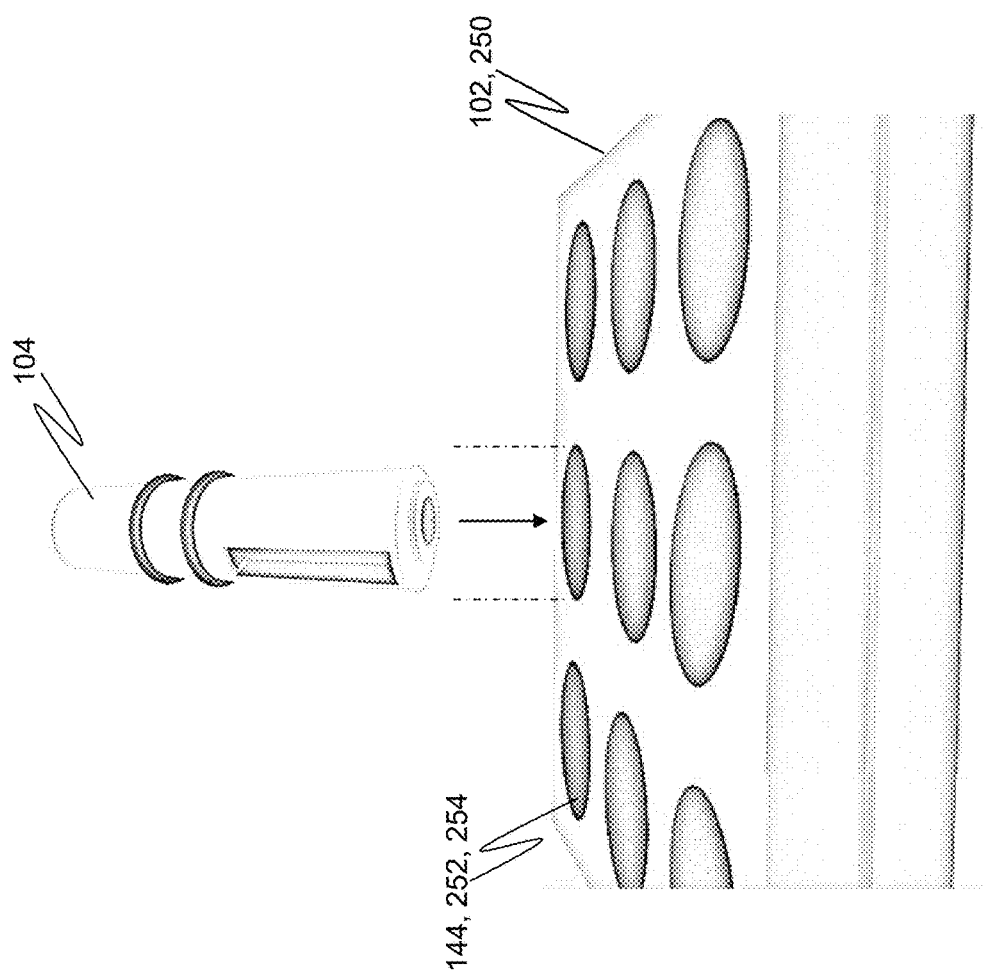

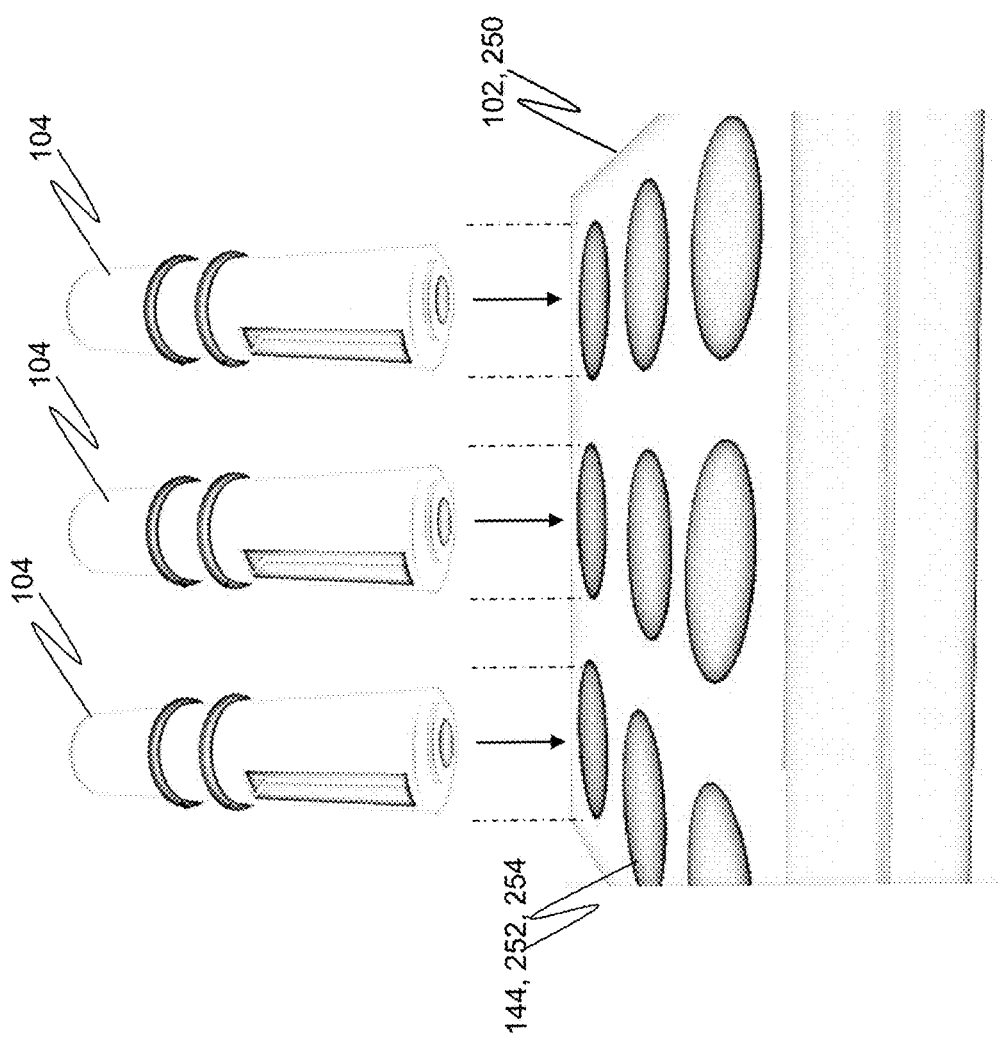

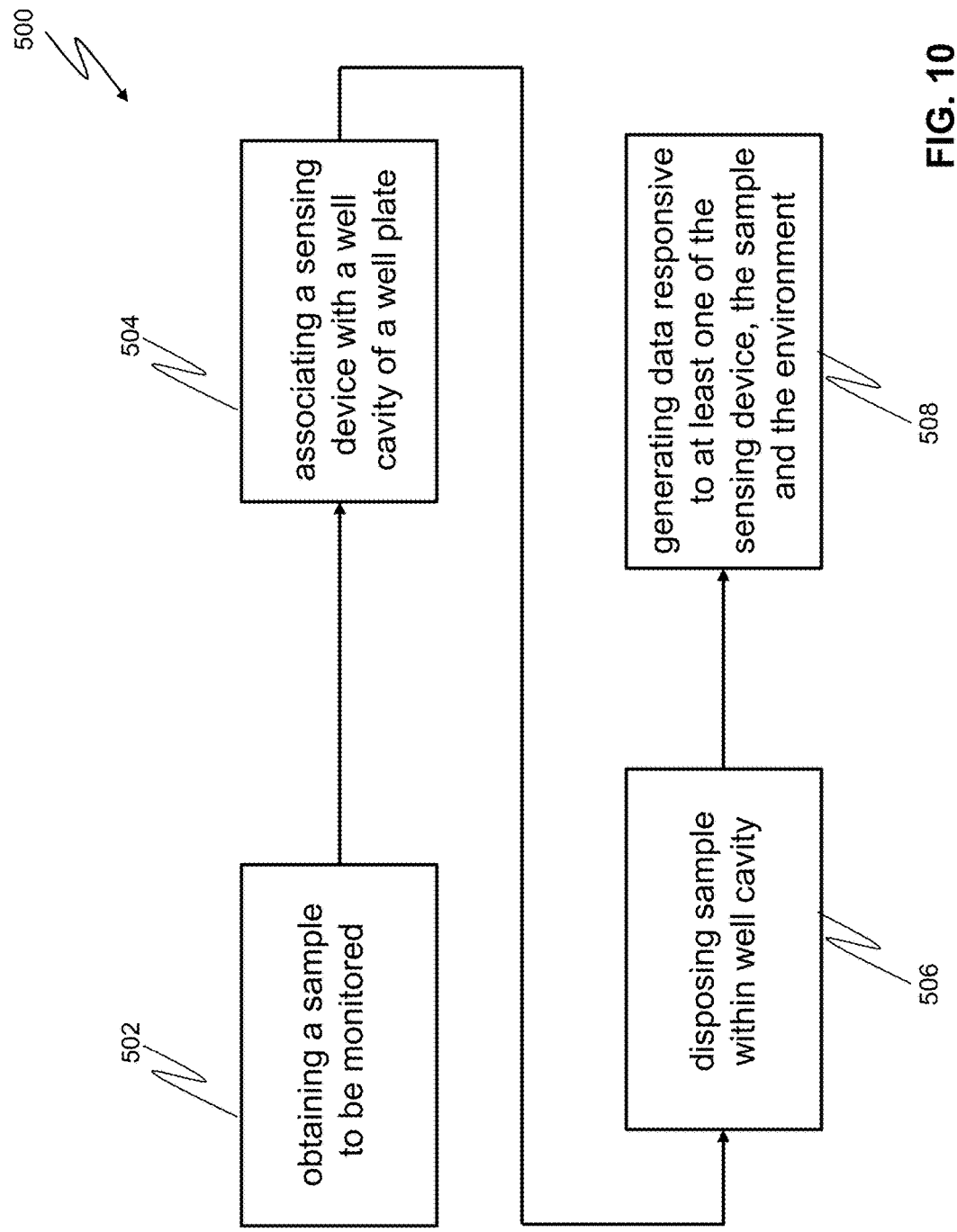

SYSTEM FOR MONITORING GROWTH MEDIA

CROSS-REFERENCE TO RELATED APPLICATIONS

This application claims the benefit of priority of the filing date of U.S. Provisional Application No. 62/155,221, entitled System for Monitoring Growth Media and filed on Apr. 30, 2015, the contents of which are incorporated by reference herein in its entirety.

FIELD OF THE INVENTION

The present invention is generally directed to monitoring growth media and more particularly directed to monitoring cell cultures for use in in vitro fertilization (IVF).

BACKGROUND OF THE INVENTION

Cell culture is a vital part of the biotechnology revolution, and is important in bringing many new and useful developments to society. During certain kinds of cell culture, in particular In Vitro Fertilization (IVF), the growth and viability of the cells is particularly sensitive to the environmental conditions during growth. Principal among these conditions are the temperature and $CO_2$ which effect the pH level of the growth media, where it has been shown that even small changes in temperature and/or $CO_2$ can adversely affect the pH levels which in turn can lead to lower chances of successful cell growth, and in the case of IVF, to a lack of success in final implantation and pregnancy. IVF generally helps couples who have difficulty conceiving, and even with the best technology, the chances for some couples successfully achieving pregnancy are low.

IVF laboratories generally grow cells in an incubator, which allows for the maintenance of a constant environment for the growing cells. The pH of growth media is frequently maintained in the incubator by controlling of the level of carbon dioxide gas which produces carbonic acid when dissolved in water. Accordingly, the more carbon dioxide present in the environment, the lower the pH of the media. Laboratories using IVF often have to remove the container of media and cells from the incubator to perform manipulations, and possibly to make measurements of characteristics such as temperature and pH within the growth media. This is undesirable because each time the cells are removed from the incubator there is a period of time in which the cells are exposed to an uncontrolled environment where they may experience changes of temperature, pH, and light, all of which affect the viability of the cells. Consequently, removal of the cells and media from the incubator removes the control of the pH provided by the regulated carbon dioxide levels in the incubator. And, if there is a problem with the carbon dioxide levels in the incubator, the pH of the media could change and threaten the viability of the cells.

Accordingly, there have been attempts to find ways to measure certain characteristics of the cells, such as pH and temperature, without having to remove the cells from the incubator. One such attempt includes obtaining an optical pH measurement via the use of dyes and/or color discs. However, while this method appears to be functional, it generally does not provide the accuracy required to adequately monitor and maintain the cells and media. This inability to accurately monitor and maintain the cells and media is undesirable because the viability of the cells and media may be negatively affected without the laboratory personnel being aware.

SUMMARY OF THE INVENTION

A system for monitoring growth media within a controlled environment is provided wherein the system includes a well plate having a well plate structure, wherein the well plate structure includes a plate top and a plate side and defining at least one well cavity, wherein the plate top includes a top opening and the plate side includes a side opening and wherein the side opening is communicated with one of the at least one well cavity. The system further includes a sensor assembly unit, wherein the sensor assembly unit includes a unit structure defining a reference material chamber containing a reference material, a sensor chamber having a chamber opening, and a base chamber. Additionally, the system includes a reference material electrode communicated with the reference material and the base chamber; a media sensor, wherein the media sensor is located within the sensor chamber to be communicated with the chamber opening and a media sensor electrode communicated with the media sensor and the base chamber, wherein the reference material electrode and media sensor electrode are communicated with a processing device.

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike in the several Figures which:

FIG. 1 illustrates a system for monitoring growth media, in accordance with one embodiment of the invention.

FIG. 2 illustrates an isometric top-side down view of the senor assembly unit for use with the system of FIG. 1, in accordance with one embodiment of the invention.

FIG. 3a illustrates a side view of the sensor assembly unit of FIG. 2, in accordance with one embodiment of the invention.

FIG. 3b illustrates a sectional view of the sensor assembly unit of FIG. 3a.

FIG. 6 illustrates a system for monitoring growth media, in accordance with an additional embodiment of the invention.

FIG. 8b illustrates a bottom up side view of the well plate of FIG. 8a.

FIG. 8d illustrates an isometric view of a sensor assembly unit and a well plate having a plurality of well cavities, in accordance with one embodiment of the invention.

FIG. 9a illustrates an isometric view of a sensor assembly unit being associated with a well plate having a plurality of well cavities, in accordance with another embodiment of the invention.

FIG. 9b illustrates an isometric view of multiple sensor assembly units being associated with a well plate having a plurality of well cavities, in accordance with another embodiment of the invention.

FIG. 10 is an operational block diagram illustrating a method for monitoring growth media and/or its environment, in accordance with one embodiment of the invention.

DETAILED DESCRIPTION

Figure 3B:
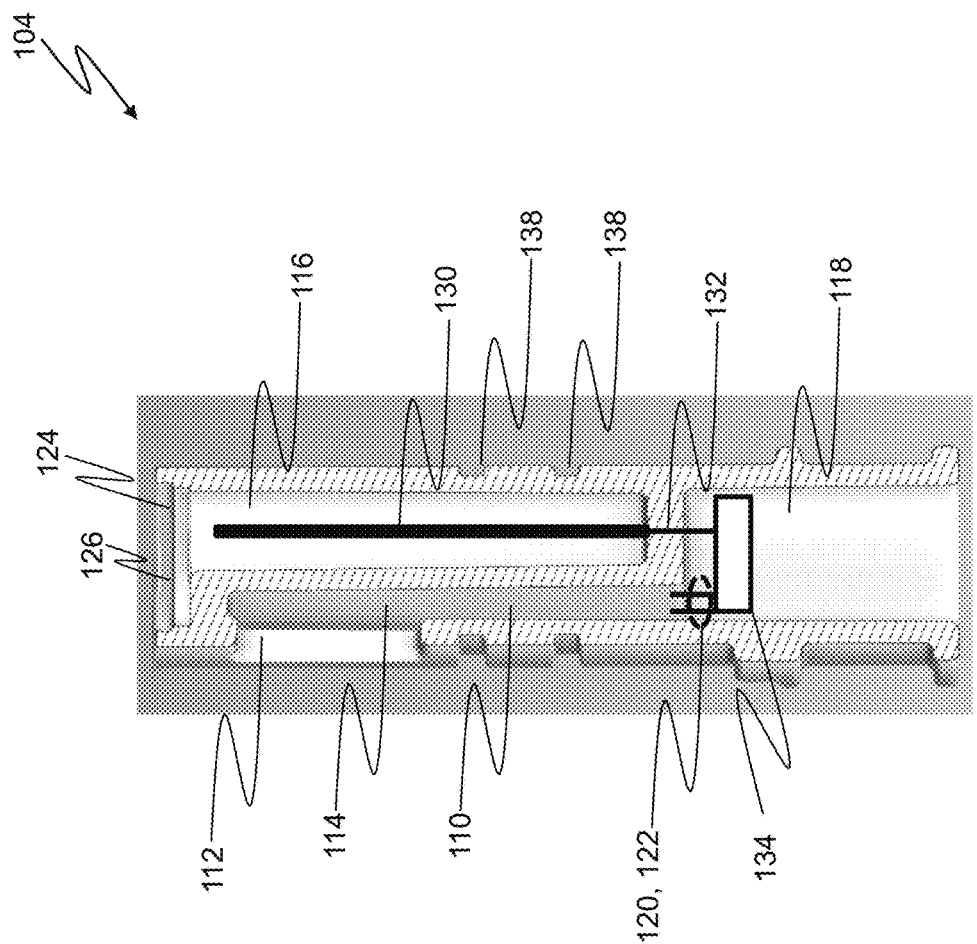
Figure 3C:
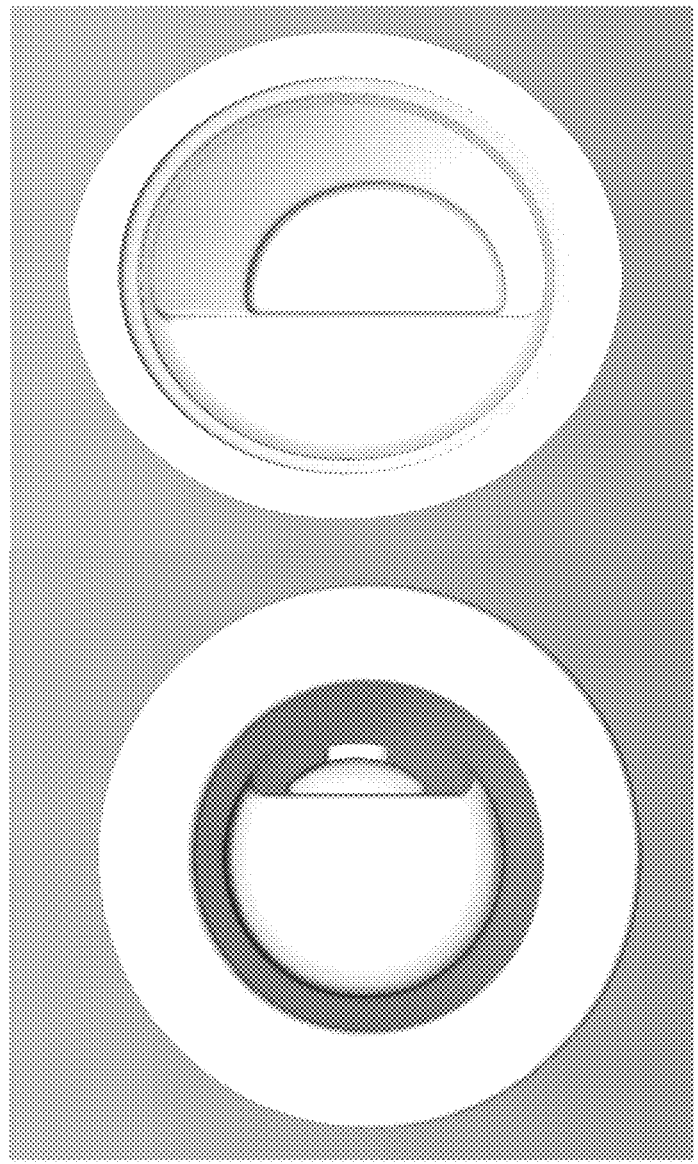
FIG. 3c illustrates a top and bottom view of the ends of the sensor assembly unit of FIG. 3a, in accordance with one embodiment of the invention.
Figure 3D:
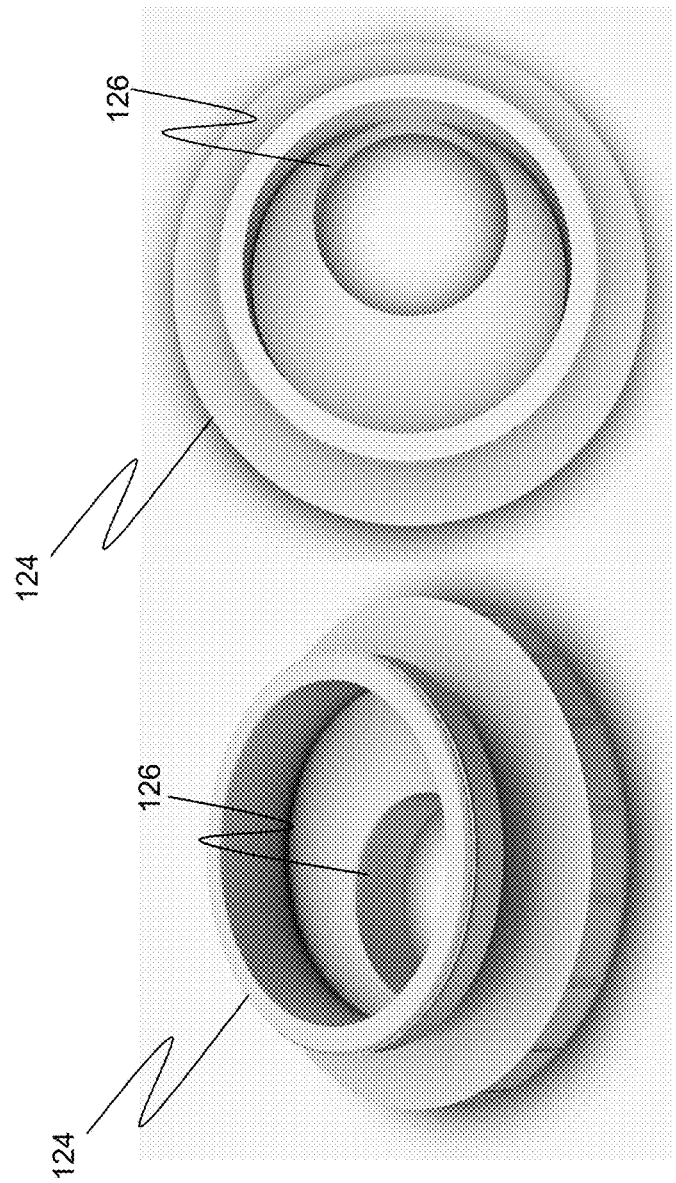
FIG. 3d illustrates a bottom and side view of a cap for the ends of the sensor assembly unit of FIG. 3a, in accordance with one embodiment of the invention
Figure 4A:
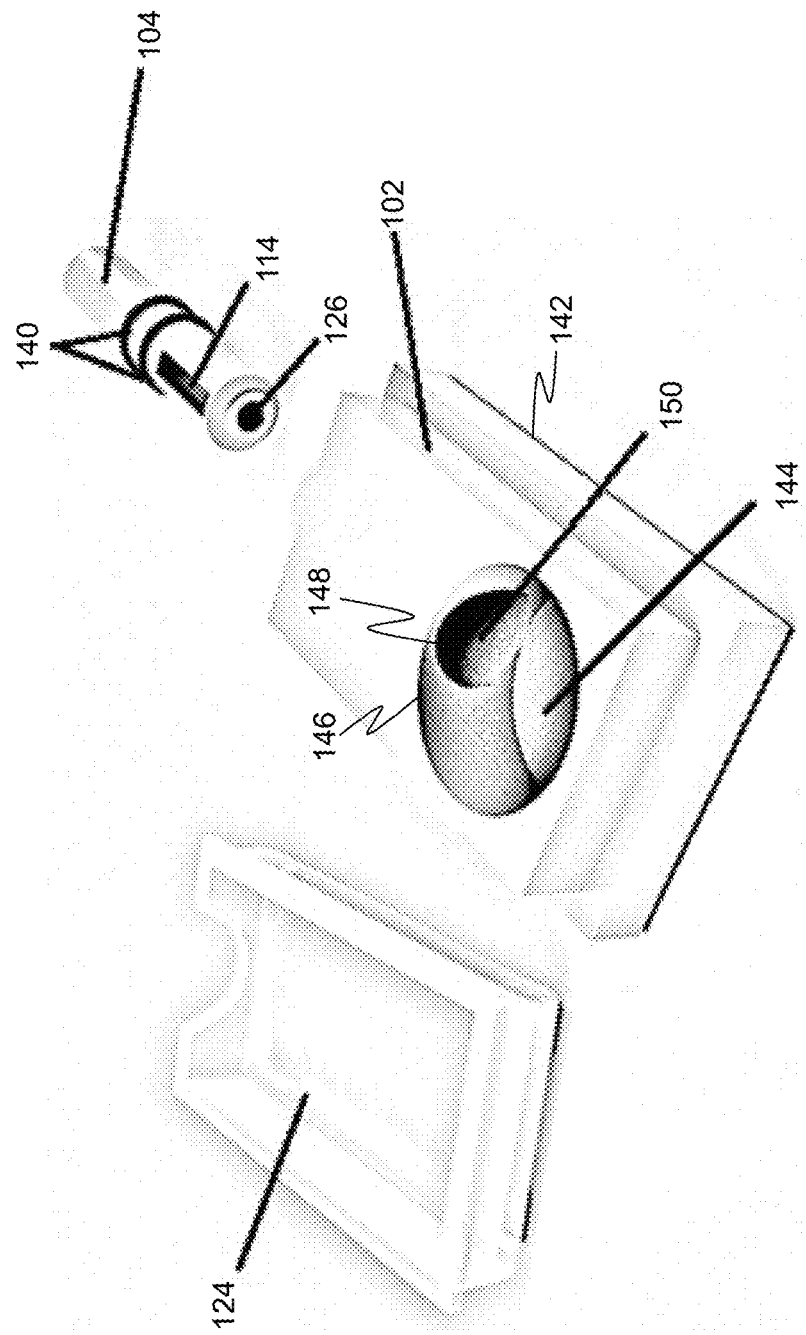
FIG. 4a illustrates an isometric top-down rear view of the well plate and sensor assembly unit of FIG. 3a, in accordance with one embodiment of the invention.
Figure 4B:
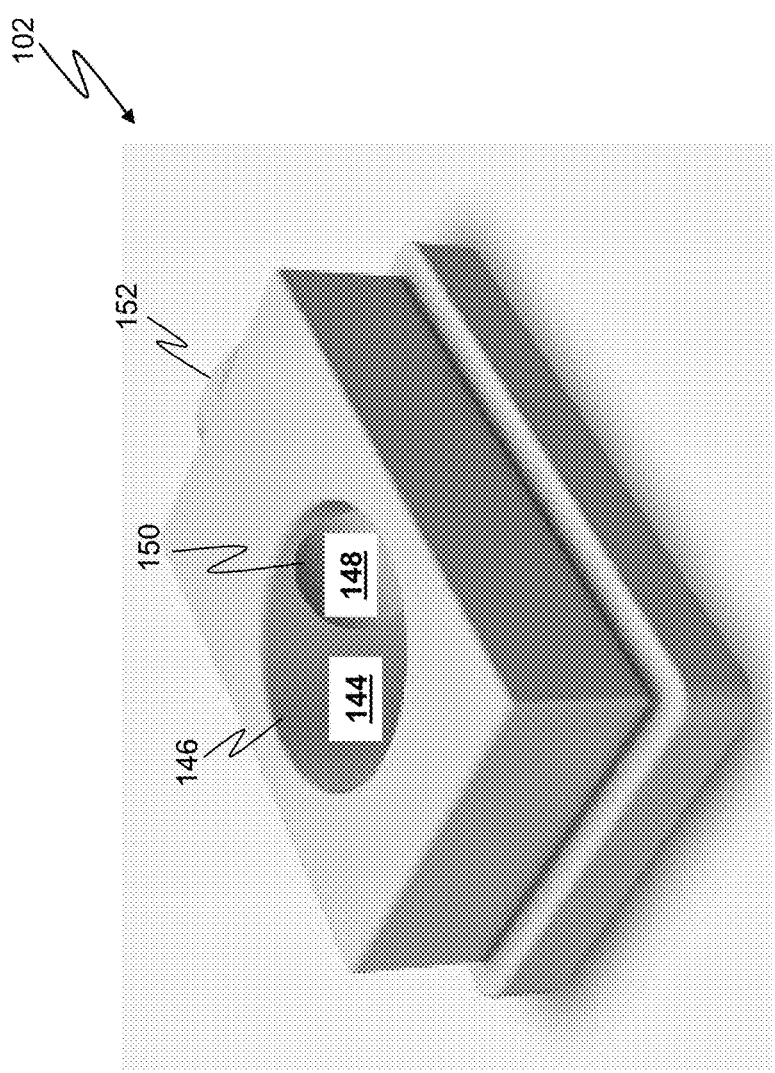
FIG. 4b illustrates a rear side view of the well plate of FIG. 4a, in accordance with one embodiment of the invention.
Figure 4C:
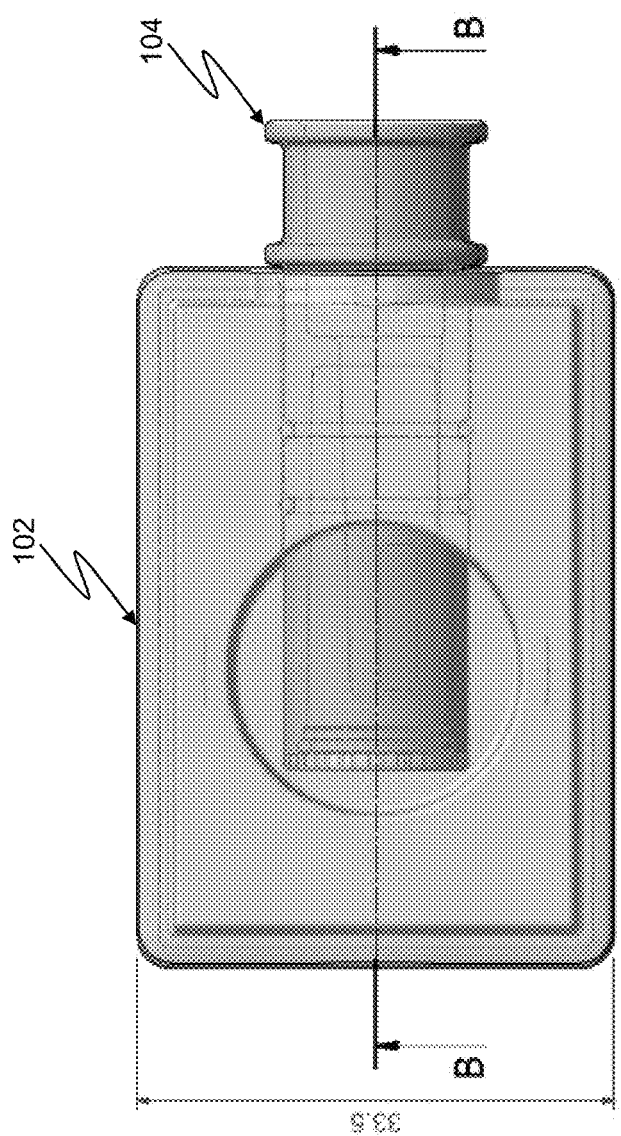
FIG. 4c illustrates a top down view of the well plate of FIG. 4a, with the sensor assembly unit of FIG. 3a located within, in accordance with one embodiment of the invention.
Figure 4D:
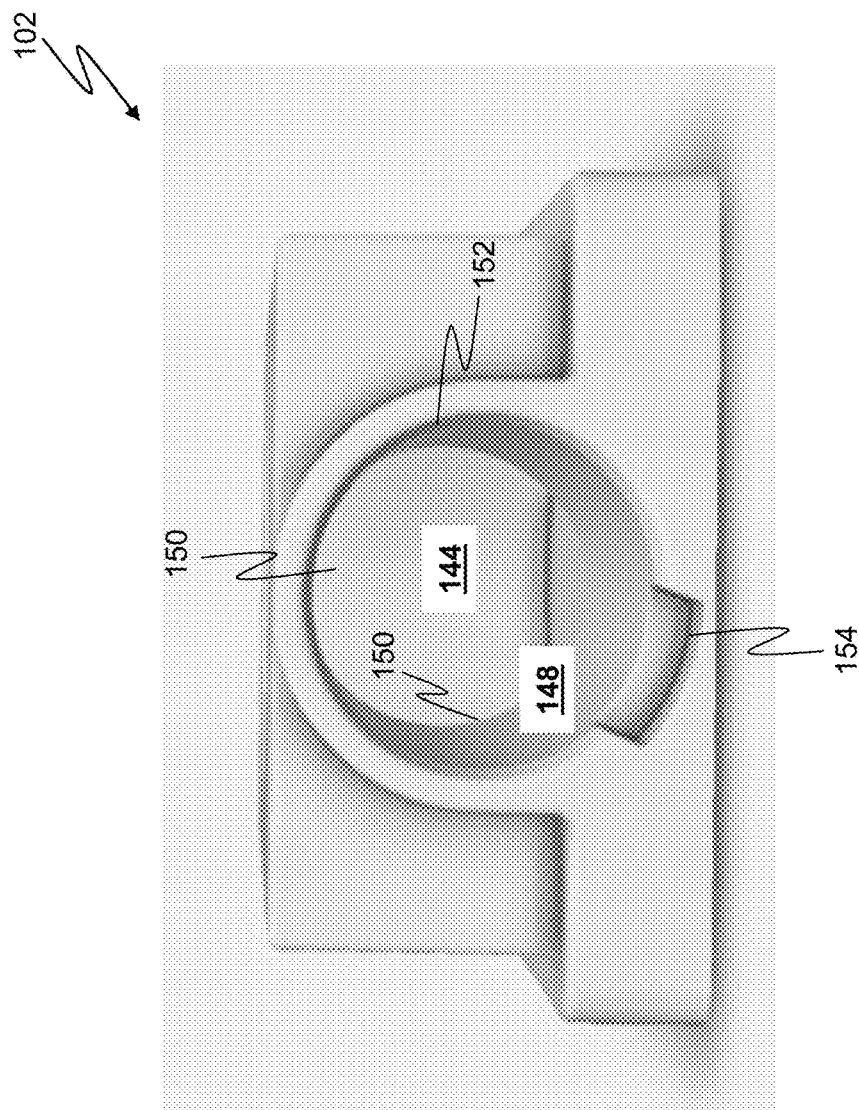
FIG. 4d illustrates a front view of the well plate of FIG. 4a showing the well plate keyed portion, in accordance with one embodiment of the invention.
Figure 5A:
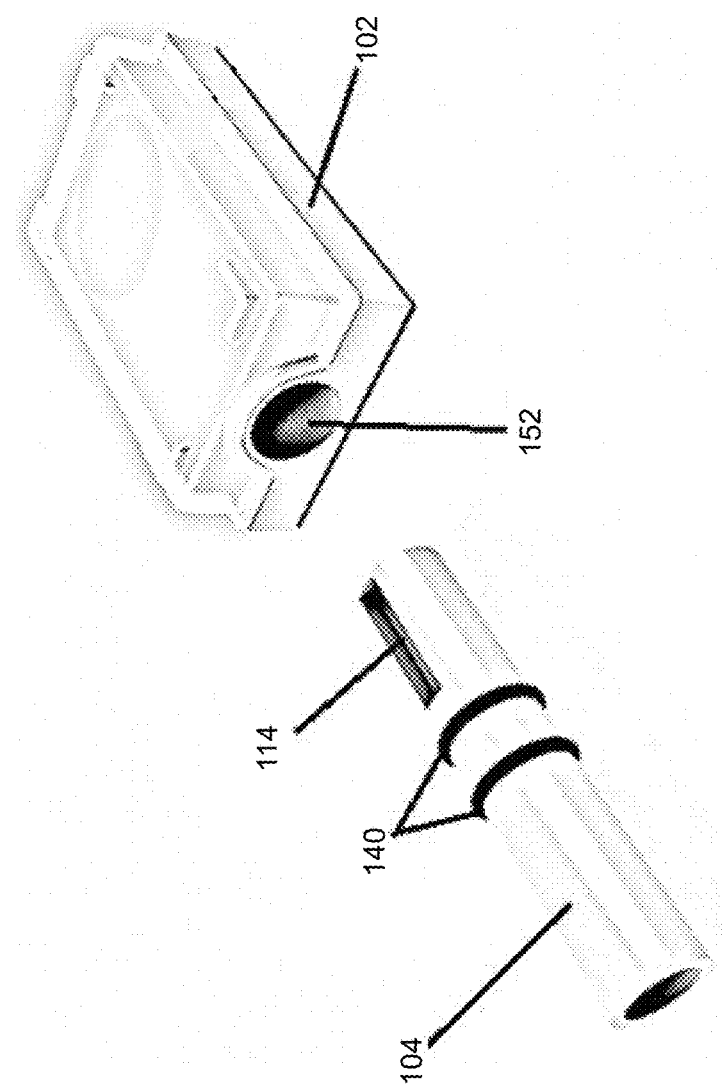
FIG. 5a illustrates a perspective view of the sensor assembly unit of FIG. 3a and the well plate of FIG. 4a, in accordance with one embodiment of the invention.
Figure 5B:
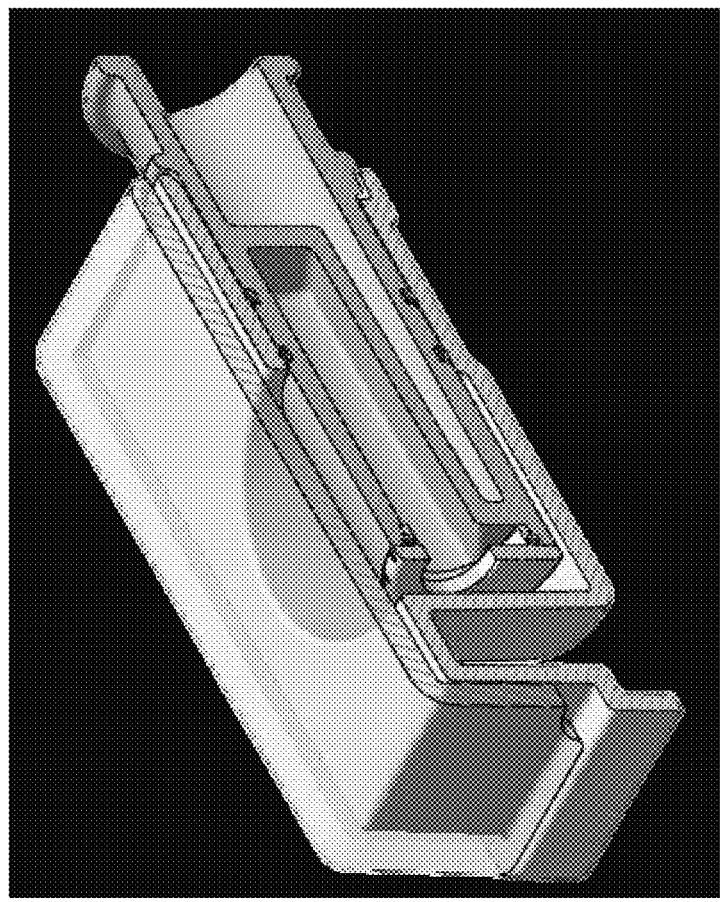
FIG. 5b illustrates a sectional view of the sensor assembly unit of FIG. 3a associated with the well plate of FIG. 4a, in accordance with one embodiment of the invention.

The present invention is directed to a system and method for monitoring growth media and cells in a controlled environment, such as an incubator. Referring to FIG. 1, one embodiment of a system 100 for monitoring growth media and cells (and/or its environment) in a controlled environment is shown, wherein the controlled environment may be within an incubator, such as for example, a low profile or mini incubator. The system 100 includes a well plate 102, at least one sensor assembly unit 104 having at least one sensor 106, and a receiver unit 108, wherein the at least one sensor 106 is communicated with the receiver unit 108 via a wireless and/or a hard-wired connection. It should be appreciated that the receiver unit 108 may be located in any place suitable to the desired end purpose, such as inside or outside of the well plate 102.

Referring to FIG. 2, FIG. 3a, FIG. 3b, FIG. 3c, and FIG. 3d, one embodiment of a sensor assembly unit 104 is shown having a cylindrical shape (but may be any shaped as desired suitable to the desired end purpose. The sensor assembly unit 104 defines a sensor chamber 110 having a sensor chamber opening 112, wherein the sensor chamber includes a sensing device 114, such as an Ion-Sensitive Field-Effect Transistor (ISFET) sensor, which is communicated with the sensor chamber opening 112. Accordingly, the sensing device 114 may be accessible via the sensor chamber opening 112. The sensor assembly unit 104 also defines a Potassium Chloride or reference chamber 116 and a wire connection chamber 118. The sensor device 114 includes a source electrode 120 and a drain electrode 122, wherein the source and drain electrodes 120, 122 extend into the wire connection chamber 118. The sensor assembly unit 104 includes a cover 124 located proximate one end of the sensor assembly unit 104, wherein the cover 124 may or may not be removable. The cover 124 may include a membrane port 126 which separates the solution to be measured from the reference chamber 116. The reference chamber 116 contains Potassium Chloride and includes a reference rod 130 (which may be constructed, as least in part, of Silver Chloride) which is at least partially disposed in the Potassium Chloride and which extends from the bottom of the reference chamber 116 toward the cover 124 (but does not contact the cover 124). The sensor assembly unit 104 may include a removable (or non-removable) cap housing the ceramic membrane port 126.

Additionally, a reference electrode 132 is provided and connected to the reference rod 130, wherein the reference electrode 132 extends into the wire connection chamber 118. It should be appreciated that the reference electrode 132 and/or the source and drain electrodes 120, 122 maybe connected to a processing device 134 which may be configured to communicate data received from the reference electrode 132 and/or the source and drain electrodes 120, 122 to a remote device. It should be appreciated the sensor assembly unit 104 includes a keyed portion 136. It should be further appreciated that in some embodiments the membrane port 126 may be constructed from any material suitable to the desired end purpose, such as a ceramic material, and/or non-ceramic materials, including polymers such as PTFE (polytetrafluoroethylene, marketed as TEFLON by Dupont, Co.). Moreover, the sensor assembly unit 104 may include depressions 138 located on an exterior portion of the sensor assembly unit 104 to allow for one or more O-Rings 140 to be associated with the exterior portion of the sensor assembly unit 104.

Referring to FIG. 4a, FIG. 4b, FIG. 4c, FIG. 4d, FIG. 5a and FIG. 5b, a well plate 102 is shown in accordance with one embodiment of the invention. The well plate 102 includes a well plate structure 142 which defines a well cavity 144 and a well cavity opening 146, wherein the well cavity opening 146 is communicated with the well cavity 144. The well plate structure 142 defines a well cavity channel 148 communicated with the well cavity 144 via a first well cavity channel opening 150. Additionally, the well plate structure 142 defines a second well cavity channel opening 152 communicated with the first well cavity channel opening 150 via the well cavity channel 148. It should be appreciated that the well cavity channel 148, the first well cavity channel opening 150 and the second well cavity channel opening 152 are sized and shaped to snugly contain the sensor assembly unit 104. In use, the end of the sensor assembly unit 104 with the membrane port 126 and sensor chamber opening 112 would be inserted into the second well cavity channel opening 152 and located within the well cavity channel 148 to extend out of the first well cavity channel 150 and into the well cavity 144.

When the sensor assembly unit 104 is located within the well cavity channel 148, the O-Rings 140 contact the inner surface of well cavity channel 148 to form a seal between the well cavity channel 148 and the sensor assembly unit 104. This prevents the media located with the well cavity 144 from leaking out of the well cavity 144 via the well cavity channel 148. Additionally, the second well cavity channel opening 152 and/or the well cavity channel 148 include a keyed portion 154 which is configured to engage with the keyed portion 136 of the sensor assembly unit 104 when the sensor assembly unit 104 is located within the well cavity channel 148. Accordingly, the sensor chamber opening 112 is disposed such that the sensing device 114 is exposed and/or in contact with the media located within the well cavity 144. Additionally, when the sensor assembly unit 104 is located within the well cavity channel 148 the end of the sensor assembly unit 104 with the wire connection chamber 118 would face out of the well plate 100 where data could be sent to a processing device and/or a storage device.

In one embodiment, the sensor assembly unit 104 may be inserted into the well plate 100 from a lateral direction (the sensor assembly unit 104 is shown partially inserted). The sensor assembly unit 104 may be communicated with a signal processor 160 which may also be communicated with temperature and humidity sensors. The signal processor 160 may be in signal communication either wirelessly or via a hard-wired connection (such as a magnetic ribbon cable) with a main PCB signal processor 162 which may be configured to communicate data either wirelessly, which can be via Bluetooth, or via a wired connection to one or more receiving device(s) 164, wherein the receiving device(s) 164 may any device suitable to the desired end purpose, such as a laptop or desktop computer, a smart phone, tablet, and/or data logging device. The data may be further communicated to a remote device via wirelessly and/or via an internet connection.

It should be appreciated that the sensor assembly unit 104 can have variable dimensions and can be constructed of a variety of materials such as plastic, metal, composite and/or a combination thereof. Additionally, the sensor assembly unit 104 may be constructed to form a seal with the well plate 100 such that liquid from the well cavity 144 being accessed does not leak out through or around the well cavity channel 148. In some embodiments the flow of liquid around or through the well cavity channel 148 may be prevented by one or more gaskets. The gaskets can take on a variety of forms such as an O-ring 140 and/or a membrane or strip. Additionally, the gaskets can be made of a variety of materials, such as rubber, plastic and/or a combination thereof.

Referring to FIG. 6, an additional embodiment of a system 200 for monitoring growth media and cells in a controlled environment is shown, where a well plate 100 may be directly associated with (such as a "piggyback" configuration) a processing device 202. Accordingly, in this configuration a hard-wired connection, such as via a ribbon cable or a wireless connection, may not be required thereby resulting in a more compact unit. The processing device 202 may be configured to send data wirelessly, such as via Bluetooth or other wireless methods, or via a hard wired connection to one or more receiving device(s) 204, wherein the receiving devices may include a computer, a smart phone, a tablet, a PDA or other any other device suitable to the desired end purpose. The data may be then be further communicated to one or more additional remote devices via wirelessly and/or via an internet connection.

Figure 7:
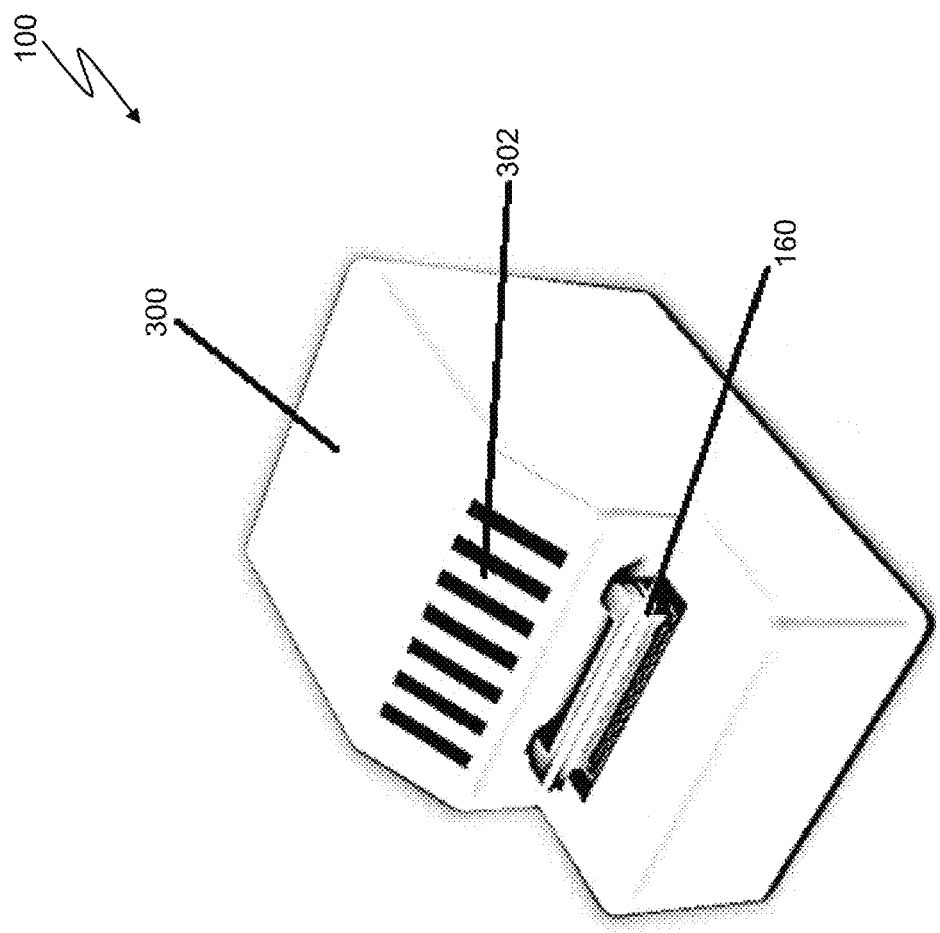
FIG. 7 illustrates a processing device for use with the system of FIG. 1 and FIG. 6, in accordance with one embodiment of the invention.
Figure 8A:
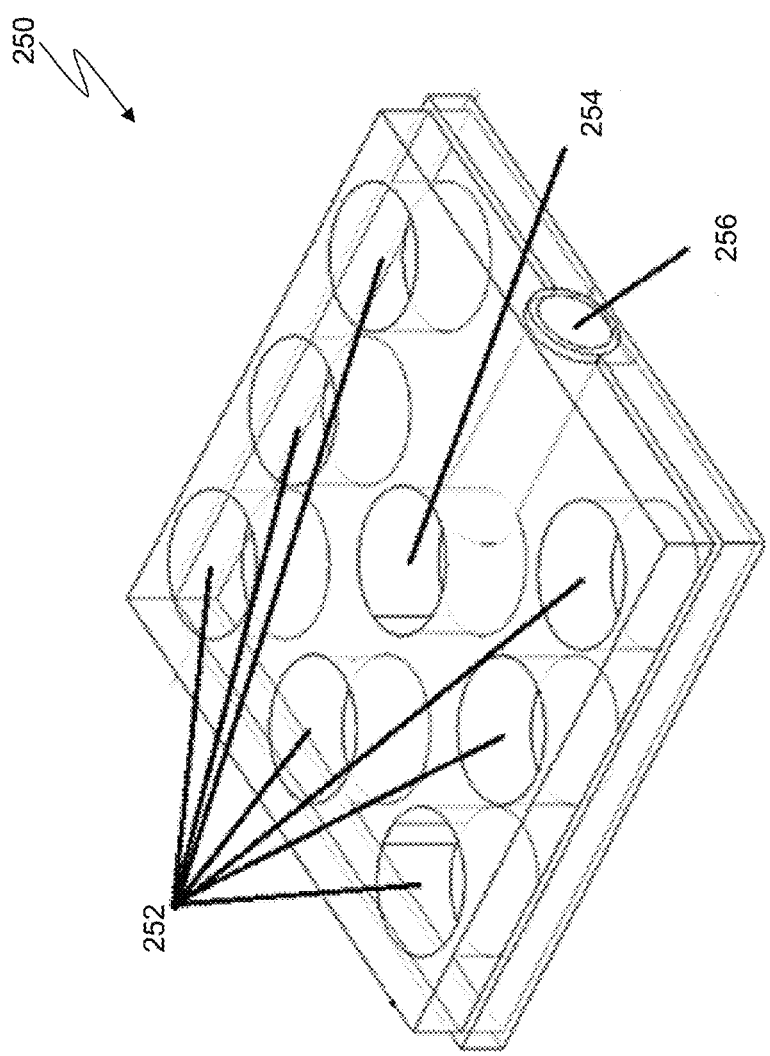
FIG. 8a illustrates a top down side view of a well plate for use with the system of FIG. 1 and FIG. 6, wherein the well plate includes a plurality of well cavities, in accordance with one embodiment of the invention.
Figure 8B:
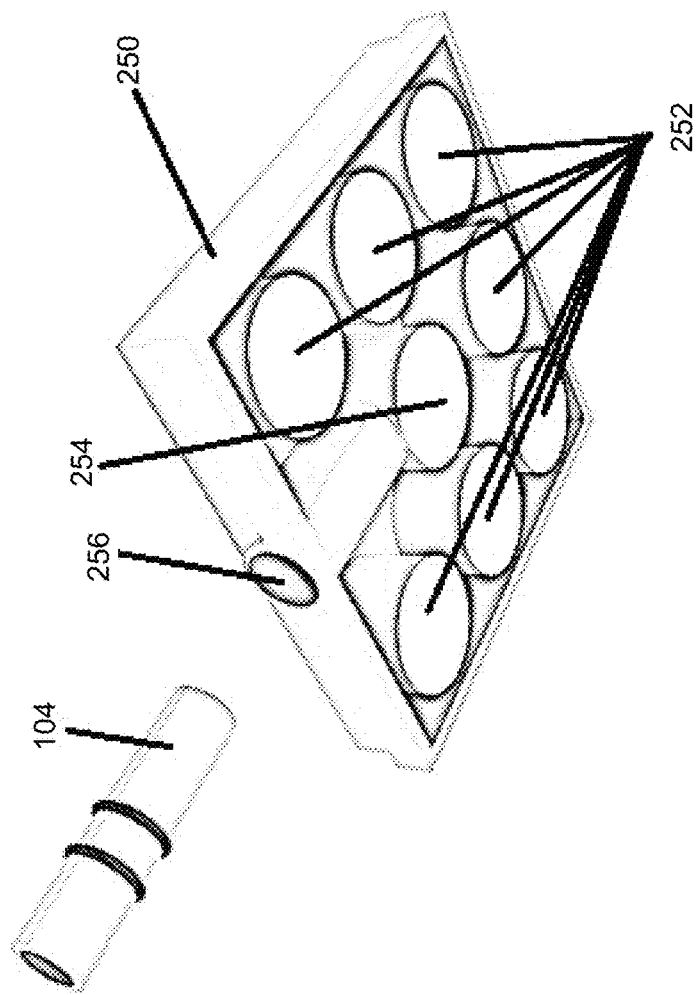
Figure 8C:
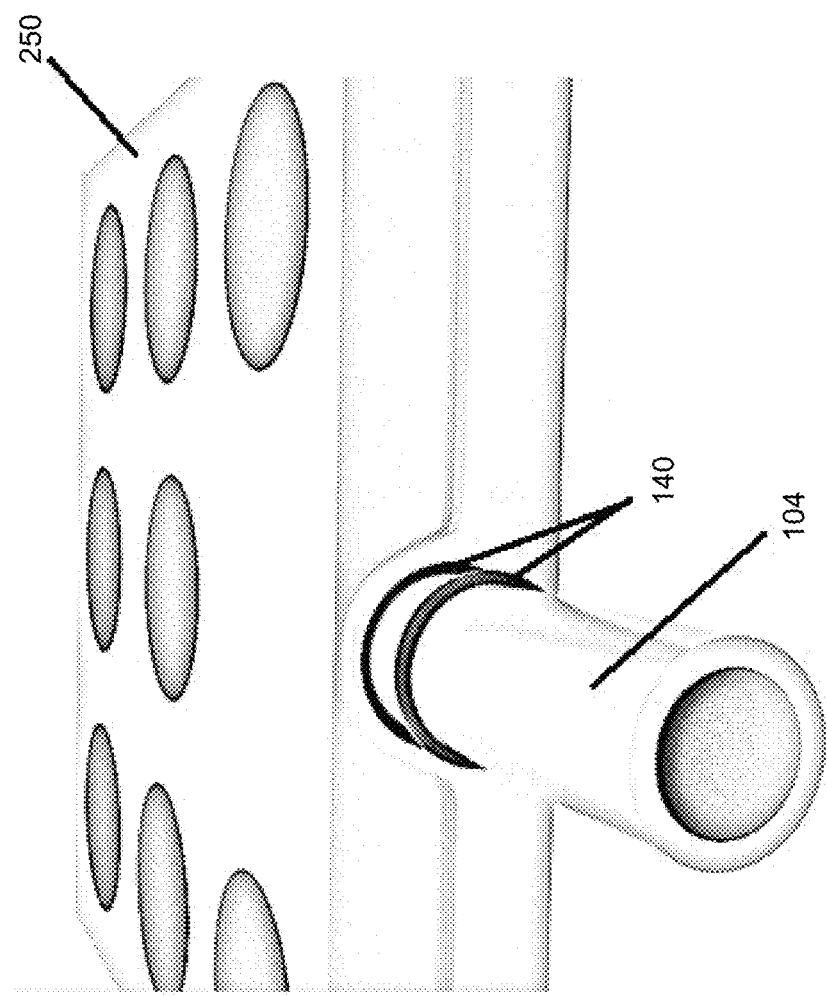
FIG. 8c illustrates a front view of the sensor assembly unit of FIG. 3a associated with the well plate of FIG. 8a having a plurality of well cavities, in accordance with one embodiment of the invention.

Referring to FIG. 7, the system 100, 200 for monitoring growth media and cells in a controlled environment may include a processing device 300, wherein the processing device 300 may include various sensors, circuitry and enclosure vents 302 that allow for the measurement of certain parameters, such as atmospheric conditions, using the various sensors located within or proximate to the processing device 300. These sensors may be configured to measure characteristics such as temperature and relative humidity, as well as levels of gases such as carbon dioxide and oxygen. Additionally, the processing device 300 may be configured for wireless and/or hard wired communications.

It should be appreciated that the well plate 102 can be described in several different embodiments, for example with variable numbers and positions of wells cavities 144, variable dimensions, and variable numbers and positions of well cavity channels 148 to accommodate one or more sensor assembly units 104. It is contemplated that the well plate 102 can have a single well cavity 144, or multiple well cavities 144. The well plate 102 and the well cavities 144 themselves may be any shape desired, such as square, rectangular, circular, and/or any other shape suitable to the desired end purpose. Additionally, the well plates 102 may be constructed of plastic, metal, composite, any other suitable material and/or any combination thereof. The well cavities 144 can be identical in size and dimensions, or different well cavities 144 in the same well plate 102 can have different size and dimensions. The well plate 102 can have a single well cavity 144 which has an aperture configured to receive at least one sensor assembly unit 104, or several of the well cavities in the well plate 102 can have such apertures. Furthermore, the well plate 102 can include a suitable lid that can be removably (or permanently) affixed to the top of the well plate 102.

Referring to FIG. 8a, FIG. 8b, FIG. 8c and FIG. 8d, an additional embodiment of a well plate 250 is shown having multiple wells cavities 252 with an open top surface, and a single well cavity 254 which is communicated with a well cavity channel 256 to accommodate a sensor assembly unit 104. This advantageously allows access by a sensor assembly unit 104 to the growth media located within the well cavity 254. As such, the well plate 250 has several wells cavities 252 without a well cavity channel 256 and one well cavity 254 with a well cavity channel 256 to allow access by a sensor assembly unit 104.

It should be appreciated that the sensor assembly unit 104 may include one or more sensors that are configured to measure characteristics such as pH, temperature, and relative humidity. The term "sensor" can include not only the tip of the sensor, but all or part of its connection with a receiver unit. At least one of the sensors is in contact with the material in one of the well cavities 144, 252, 254 of the well plate 100, 250. In some embodiments, the sensor or sensors contact the material in a well cavity 144, 252, 254 that contain growth media but no actual cells. In such embodiments, the measurement of the characteristics in the well plate 102, 250 of growth media with no cells may be used to approximate the conditions within in the well cavities 144, 252, 254 which may contain growth media plus cells. Additionally, in some embodiments, at least one sensor measures pH, wherein the pH sensor may be an ISFET and/or other pH measuring device. It should be appreciated that an ISFET is a very sensitive sensor for measuring pH, and is more accurate and subject to less drift than other pH measuring methods such as optical methods. Unlike optical methods, an ISFET typically requires the sensor to contact the material or media it is measuring.

It should be appreciated that once the sensor assembly unit 104 is securely located within the well plate 102, 250 such that the O-rings 140 act as a seal between the sensor assembly unit 104 and the inner wall of the well cavity channel 148. The growth media is then located within the well cavity(s) 144, 252, 254 and the cover 124 is attached to enclose the wells cavities 144, 252, 254.

It should be appreciated that the keyed portions of the sensor assembly unit 104 and the well plate 102, 250 advantageously acts to align the sensing device 114 within the sensor assembly unit 104 with the media within the well cavity 144, 252, 254. This works to make sure the sensing device 114 is in contact with the growth media within the well cavity 144, 252, 254 and to prevent air from coming into contact with the sensing device 114 when the well cavity 144, 252, 254 is filled.

It should be appreciated that the present invention is illustrated herein as the sensor assembly unit 104 being inserted into the well plate 102, 250 via a side portion of the well plate 102, 250. It is contemplated that other physical arrangements of the invention are contemplated. For example, the sensor assembly unit 104 may be associated with the well plate 102, 250 via the top of the well plate 102, 250 (See FIG. 9*a* and FIG. 9*b*) or via the bottom of the well plate 102, 250. This may advantageously allow for a single well 144, 252, 254 and/or multiple wells 144, 252, 254 to be monitored simultaneously. Additionally, it would advantageously allow for a specific well 144, 252, 254 or wells 144, 252, 254 to be monitored as desired. Furthermore, it is contemplated that the sensor assembly unit 104 (and/or the functionality of the sensor assembly unit 104) may be integrated into the well plate.

Referring to FIG. 10, an operational block diagram illustrating a method 500 for monitoring growth media is shown in accordance with one embodiment of the invention, and includes obtaining a sample to be monitored, as shown in operational block 502. This may be accomplished by obtaining a cell culture or other organism of interest that is to be grown and/or monitored. The method includes associating a sensing device 114 with a well cavity 144, 252, 254 of a well plate 102, 250, as shown in operational block 504, and disposing the sample of interest to be monitored within the well cavity 144, 252, 254, as shown in operational block 506, such that the sensing device 114 is exposed to the sample of interest to be monitored. The method further includes generating data responsive to the sensing device 114 and/or at least one of the sample of interest to be monitored and the environment containing the sample of interest to be monitored, as shown in operational block 508. It should be appreciated that the sensing device 114 may be configured to generate data responsive to at least one of the sample to be monitored and/or the environment containing the sample to be monitored. It should be further appreciated that the method of the invention may be practiced in any order desired and/or suitable to the desired end result.

It should be appreciated that the present invention may be used with any cell and/or organism that requires a growth media and/or that need a pH balance. Moreover, it should be further appreciated that the sensor assembly unit 104 does not have to be limited to measurement of pH, temperature and/or relative humidity. Rather the sensor assembly unit 104 (or other sensors located within the incubator/environment) may be configured to measure, monitor or sense any parameter desired. Accordingly, additional sensors such as CO2 and/or O2 sensors may be included and would provide additional quality control capability for any cell growth environment where the health of the cell growth is dependent upon contributing factors. Some of these contributing factors may include Temperature RH, CO2, O2 and or pH levels, just to name a few. It should be appreciated that, in one embodiment, these additional sensors would allow for feedback to determine whether the sensors are working correctly. For example, because pH level is directly proportional to the CO2 level, the data from the pH sensor and the CO2 sensor should correspond with each other. If it doesn't then that might be an indication that one (or more) of the sensors is not functioning correctly or that another issue or problem exists with the media and/or environment.

Additionally, it is contemplated that the sensor or sensors may have a wireless or a hard wired connection with a processor unit that can be located inside or outside of the incubator, wherein the processor unit may be configured to receive the information from the sensors and send the data to a receiving device. In some embodiments, multiple processing devices may be provided, wherein an initial signal processor device sends data to a main processor which may then send the data to the receiving device. The data can be sent by wired or wireless means. In one embodiment, the data may be sent wirelessly in Bluetooth format.

Furthermore, it is contemplated that the receiving device may be a PDA, computer, tablet computer, or smartphone. Additionally, the receiving device can be the final terminus of the data, or it can push the data to a further destination, such as another electronic component or the internet.

In some embodiments, the data may be used to track the conditions in the growth media over time, to determine for example if the cells are likely to be viable. The system may also include a feedback loop. In such an embodiment, the data may be part of a homeostatic system, in which the measurement of a characteristic is used to send information to change the conditions within the incubator to maintain homeostasis. For example, in an embodiment, measurement of pH is used to alter the amount of a pH regulating substance, such as the amount of carbon dioxide in an incubator.

While the invention has been described with reference to an exemplary embodiment, it should be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

I claim:

1. A system for monitoring growth media within a controlled environment, the system comprising:
   a well plate, wherein the well plate includes a well plate structure having a plate top and a plate side and defining at least one well cavity, wherein the plate top includes a top opening and the plate side includes a side opening and wherein the side opening is communicated with one of the at least one well cavity;
   a sensor assembly unit, wherein the sensor assembly unit includes a unit structure defining a reference material chamber containing a reference material, a sensor chamber having a chamber opening, and a base chamber;
   a reference material electrode communicated with the reference material and the base chamber;
   a media sensor, wherein the media sensor is located within the sensor chamber to be communicated with the chamber opening; and
   a media sensor electrode communicated with the media sensor and the base chamber, wherein the reference material electrode and media sensor electrode are communicated with a processing device,
   wherein the side opening is configured to receive and contain the sensor assembly unit, and wherein the side opening includes a side opening keyed portion and the unit structure includes a unit structure keyed portion, wherein the side opening keyed portion and the unit structure keyed portion are configured such that the sensor assembly unit is contained within the side opening in a predetermined orientation.

2. The system of claim 1, wherein the reference material electrode and media sensor electrode extend into base chamber.

3. The system of claim 1, wherein the side opening keyed portion and the unit structure keyed portion are configured such that when the sensor assembly unit is located within the side opening, the media sensor is communicated with the growth media.

4. The system of claim 1, further including at least one O-ring disposed to be located between the well plate and the sensor assembly unit.

5. The system of claim 4, wherein one of the at least one O-ring is located on an external portion of the unit structure when the sensor assembly unit is disposed within the side opening.

6. The system of claim 1, wherein the at least one well cavity includes a plurality of well cavities.

7. The system of claim 1, wherein the media sensor is a pH sensor.

8. The system of claim 1, wherein the media sensor is an Ion-Sensitive Field-Effect Transistor (ISFET).

9. The system of claim 1, wherein the processing device is configured to receive data from the reference material electrode and media sensor electrode and communicate the data to a receiving device.

10. The system of claim 1, further comprising a well plate cover, wherein the well plate cover is removably associated with the well plate to cover the at least one well.

* * * * *